(12) United States Patent
Hori et al.

(10) Patent No.: US 6,899,687 B2
(45) Date of Patent: May 31, 2005

(54) MASSAGE MACHINE AND PHYSIOLOGICAL QUANTITY MEASURING CIRCUIT FOR USE IN THE MACHINE

(75) Inventors: Kunihiko Hori, Hirakata (JP); Yoshihisa Fujiwara, Uji (JP); Kazuya Hiyamizu, Hirakata (JP); Toshiki Koma, Himeji (JP); Torahiko Nonoue, Kakogawa (JP)

(73) Assignee: Sanyo Electric Co., Ltd., Moriguchi (JP)

( * ) Notice: Subject to any disclaimer, the term of this patent is extended or adjusted under 35 U.S.C. 154(b) by 0 days.

(21) Appl. No.: 10/085,135

(22) Filed: Mar. 1, 2002

(65) Prior Publication Data

US 2002/0123704 A1 Sep. 5, 2002

(30) Foreign Application Priority Data

Mar. 1, 2001 (JP) ...................................... 2001-056877
Mar. 1, 2001 (JP) ...................................... 2001-056878

(51) Int. Cl.⁷ ............................................... A61H 7/00
(52) U.S. Cl. .............................. 601/1; 601/46; 601/84; 601/99; 601/100; 601/102; 601/103
(58) Field of Search .............................. 601/15, 46, 49, 601/51–52, 56–60, 70, 84, 86, 90, 98, 99, 100, 102, 103, 115, 116, 1; 600/26–28; 128/905

(56) References Cited

U.S. PATENT DOCUMENTS 5,304,112 A * 4/1994 Mrklas et al. ................. 601/15
5,957,854 A * 9/1999 Besson et al. ............... 600/509
5,993,401 A * 11/1999 Inbe et al. ..................... 601/46
6,024,575 A * 2/2000 Ulrich ......................... 128/905
6,117,094 A * 9/2000 Fujii ............................. 601/99
6,371,123 B1 * 4/2002 Stark et al. ................... 601/23
6,494,850 B1 * 12/2002 Kitadou et al. ............... 601/49

FOREIGN PATENT DOCUMENTS

| JP | 04-180730 | 6/1992 |
|----|-----------|--------|
| JP | 6-209 | 1/1994 |
| JP | 06-000209 | 1/1994 |
| JP | 08-024232 | 1/1996 |
| JP | 09-047480 | 2/1997 |
| JP | 9-75413 | 3/1997 |
| JP | 2000-014656 | 1/2000 |

* cited by examiner

Primary Examiner—Danton D. DeMille
Assistant Examiner—Quang D. Thanh
(74) Attorney, Agent, or Firm—Armstrong, Kratz, Quintos, Hanson & Brooks, LLP

(57) ABSTRACT

The invention provides a massage machine for health care which comprises a living body information sensor 5 for detecting living body information of the autonomic nervous system of the person to be massaged, a control circuit 6 for judging the psychological state of the person based on the living body information detected, and a memory 61 for holding histories of psychological states of persons to be massaged. The machine is adapted to judge the physical condition of the person based on the history of psychological states of the person, and to judge whether the condition of the person's health is improved by massage so as to utilize the result of judgement as guidelines for health care.

5 Claims, 16 Drawing Sheets

FIG.6

| JUDGMENT | GSR | SKIN TEMP. | PULSE |
|---|---|---|---|
| RELAXED | $\Delta G \leq -A/\text{SEC}$ | $\Delta T < 0$ | $\Delta H < 0$ |
|  | $\Delta G \leq -A/\text{SEC}$ | $\Delta T \geq 0$ | $\Delta H < 0$ |
|  | $\Delta G \leq -A/\text{SEC}$ | $\Delta T \geq 0$ | $\Delta H \geq 0$ |
|  | $-A/\text{SEC} < \Delta G \leq +B/\text{SEC}$ | $\Delta T \geq 0$ | $\Delta H < 0$ |
| NEUTRAL | $\Delta G \leq -A/\text{SEC}$ | $\Delta T < 0$ | $\Delta H \geq 0$ |
|  | $-A/\text{SEC} < \Delta G < +B/\text{SEC}$ | $\Delta T < 0$ | $\Delta H < 0$ |
|  | $-A/\text{SEC} < \Delta G < +B/\text{SEC}$ | $\Delta T \geq 0$ | $\Delta H \geq 0$ |
|  | $+B/\text{SEC} < \Delta G < +C/\text{SEC}$ | $\Delta T \geq 0$ | $\Delta H < 0$ |
| ACTIVE | $-A/\text{SEC} < \Delta G < +B/\text{SEC}$ | $\Delta T < 0$ | $\Delta H \geq 0$ |
|  | $+B/\text{SEC} < \Delta G < +C/\text{SEC}$ | $\Delta T < 0$ | $\Delta H < 0$ |
|  | $+B/\text{SEC} < \Delta G < +C/\text{SEC}$ | $\Delta T \geq 0$ | $\Delta H \geq 0$ |
| PAIN | $+B/\text{SEC} < \Delta G < +C/\text{SEC}$ | $\Delta T < 0$ | $\Delta H \geq 0$ |
|  | $\Delta G \geq +C/\text{SEC}$ | don't care | don't care |

Figures (0 – 100) given to marks are subjective values of shoulder stiffness.

0 : NO SENSATION OF STIFFNESS IN SHOULDER

100 : VERY STIFF SHOULDER SENSED

ESTIMATED SENSATION OF STIFFNESS

ESTIMATED DEGREE OF LUMBAGO

MASSAGE MACHINE AND PHYSIOLOGICAL QUANTITY MEASURING CIRCUIT FOR USE IN THE MACHINE

FIELD OF THE INVENTION

The present invention relates to massage machines adapted to give one or some kinds of massages to various parts of the user, and more particularly to massage machines for health care which are adapted for the health care of the user and to physiological quantity measuring circuits for use in the massage machine which are adapted to detect physiological quantities of the autonomic nervous system of the user by physiological quantity sensors such as a skin temperature sensor and perspiration quantity sensor and to thereby control the massage operation of the machine based on the detected physiological quantities.

BACKGROUND OF THE INVENTION

With reference to FIG. 1, massage machines generally comprise a chair body 10 including legs 11, a seat 12, a backrest 13 and a pair of opposite armrests 14, 14, and a massage mechanism 2 having a plurality of therapeutic members 21 and incorporated into the body 10. The therapeutic members 21 are reciprocatingly moved up and down while being vibrated, whereby the human body is massaged.

The massage machines of the type mentioned include one which is adapted to detect a stiff body part before giving a massage so as to massage the most appropriate part concentrically [JP-A No. 9-75413(1997)]. This machine is capable of giving a massage concentrically to the stiff part of the user.

However, the conventional machine is unable to detect the psychological state of the user such as "comfort" or "pain," is therefore unable to detect whether the condition of the user's health is improved by an effective massage actually given to the user, and further has the problem of failing to give an effective massage for realizing an enhanced degree of relaxation or increased refreshment.

Accordingly, a massage machine is proposed which is adapted to detect physiological quantities (relaxation indicating factors) of the person to be massaged, such as pulse, skin temperature and galvanic skin response (GSR), for controlling a massage mechanism in accordance with the degree of relaxation of the person [JP-A No. 6-209(1994)]. In giving a specified massage to a particular part, the massage machine is capable of detecting the psychological state of the user by monitoring variations in physiological quantities of the user, so that an effective massage can be performed to realize an increased degree of relaxation or refreshment.

Massage machines give different kinds of massages, such as tapping, kneading, combination of these movements and rolling, to a plurality of parts such as the shoulder, back, waist and leg. Different parts massaged and different kinds of massages given produce different variations in the physiological quantities of the user. When massages are given to various body parts, variations in the skin temperature or GSR of the person massaged are detected, and the psychological state of the user as given each massage at a particular part is detected based on the variation.

However, a sufficiently high correlation is not always available between the psychological state detected by performing a certain massage by the conventional machine on a particular part of the user and the psychological state subjectively explained by the user. Consequently, the machine has the problem of failing to give effective massages.

SUMMARY OF THE INVENTION

A first object of the present invention is to provide a massage machine for health care which is capable of judging whether the massage given to the user serves to improve the condition of the user's health and utilizing the result of judgement as guidelines for health care.

A second object of the present invention is to provide a physiological quantity measuring circuit for use in a massage machine adapted to give different kinds of massages to various parts of the user, the circuit being capable of accurately detecting the psychological state of the user from the user's physiological quantities.

To fulfill the first object, the present invention provides a massage machine for health care comprising a living body information sensor for detecting the living body information of the autonomic nervous system of the person to be massaged, means for judging the psychological state of the person based on the living body information detected, and means for holding histories of psychological states of persons to be massaged.

The massage machine of the invention is adapted to judge the psychological state of the person to be massaged, such as "comfort" or "pain," based on the living body information of the autonomic nervous system of the person, so that the physical condition of the person can be detected with reference to the history of psychological state judged. For example, if the psychological state of having "pain" continues, this indicates that the physical condition is not remedied despite the massage, while if the psychological condition changes from "pain" to "comfort," this indicates the amelioration of the physical condition. Accordingly, it is possible to judge whether the condition of the person's health is improved by the massage given and to utilize the result of judgement as guidelines for health care.

Stated more specifically, the living body information sensor includes one or more sensors selected from among a GSR (galvanic skin response) sensor, a pulse sensor and a skin temperature sensor. It is known that the living body information detected by these sensors varies with the degree of relaxation or tension. When in a relaxed condition, the person exhibits a low activity value, while when tense, he exhibits a high value in activity. Accordingly, the psychological state of the person, such as a sensation of stiffness or physical condition, can be estimated with high reliability from the variations in the living body information detected by these sensors.

For example, when the living body information sensor comprises a pulse sensor, a drop in the pulse rate can be interpreted as indicating a relaxed state ("comfortable" state), whereas a rise in the pulse rate can be interpreted as indicating a tense state (state of having "pain"). Alternatively when the living body information sensor comprises a skin temperature sensor, a rise in skin temperature can be interpreted as indicating a relaxed state, while a drop in the skin temperature a tense state. Further when the living body information sensor comprises a GSR sensor, a reduction in GSR can be interpreted as indicating a relaxed state, while a rise in GSR a tense state.

Further stated more specifically, the history holding means comprises means for counting the frequency with which the person is judged to be in a tense state when massaged at each of different body parts, and the count obtained by the counting means is held as a history of psychological state. A count which is relatively greater can be interpreted as indicating an impaired physical condition, while a count which is relatively smaller can be interpreted as conversely indicating an ameliorated physical condition. With an embodiment comprising means for displaying variations in the count involved in massaging particular one of the body parts, the tendency of variations in the count can be quantitatively determined, so that variations in physical condition can be judged more reliably.

Thus, the massage machine of the invention for health care is capable of judging whether the condition of the person's health is ameliorated by massages so as to utilize the result of judgement as guidelines for health care.

In order to accomplish the second object, we have clarified why the conventional massage machine fails to provide a sufficiently high correlation between the psychological state detected by giving a certain massage to a particular part of the user and the psychological state subjectively explained by the user, as will be described below. With the conventional massage machine, the output signal of a thermistor for detecting the skin temperature is converted to voltage by one signal detector, and the output signal of a GSR electrode for detecting the quantity of perspiration is converted to voltage by one signal detector, detecting variations in skin temperature or GSR based on the output signals of the two signal detectors. These signal detectors need to produce a required output voltage over a wide range in conformity with variations in skin temperature or GSR, and therefore have such signal conversion characteristics that the variations in output signal are small relative to variations in input signal, failing to achieve sufficiently high detection accuracy.

For example, variations are greater in skin temperature than in body temperature, so that when it is attempted to obtain an output voltage in the range of 0 V to 5 V for the range of 15° C. to 38° C., the signal conversion characteristics are 0.22 V per degree C. Further in the case of GSR, variations are as great as tens of kiloohms to thousands of kiloohms, and when a sufficient output voltage is to be obtained over such a wide range, the signal conversion characteristics become nonlinear. Although relatively great output voltage variations are available, for example, over the range of 0 to 1000 kΩ, output voltage variations for about 2000 kΩ are much smaller than for about 50 kΩ (for example, about ⅐), hence impaired measurement accuracy.

Improved measurement accuracy can be obtained by constructing the physiological quantity detecting circuit in a multiplicity of stages to obtain different kinds of signal conversion characteristics which differ in the relationship of the output signal to the input signal as shown in FIG. 15 or 16 for the selective use of appropriate kind of signal conversion characteristics in accordance with the magnitude of input signal, so that each kind of signal conversion characteristics involves increased variations in output signal relative to the input signal.

However, when this method is used, it is likely that the signal conversion characteristics will be changed over from one kind to another for use in signal conversion processing in accordance with a variation of input signal while giving same kind of massage to the same part. Since different kinds of signal conversion characteristics involve different errors, the difference in error then appears as a variation in output signal to result in lower accuracy in measuring physiological quantities.

Accordingly, the physiological quantity measuring circuit for use in the massage machine of the invention comprises a physiological quantity detection circuit for converting an output signal from a physiological quantity sensor to a physiological quantity detection signal. The detection circuit comprises a plurality of signal converters exhibiting different kinds of signal conversion characteristics which are different in the relationship of the output signal with the input signal. These different kinds of signal conversion characteristics overlap each other with respect to the range of input signals to be processed by the converter for signal conversion.

The measuring circuit comprises a signal processing circuit for producing physiological quantity data based on a physiological quantity detection signal obtained from the detection circuit. The signal processing circuit produces a series of items of physiological quantity data in the process of giving the same massage to the same body part based only on physiological quantity detection signals resulting from one of the different kinds of signal conversion characteristics of the detection circuit when the resulting detection signals are all included within an effective output range of said one kind of signal conversion characteristics, or to produce a series of items of physiological quantity data in the process based on physiological quantity detection signals resulting from one kind of or the different kinds of signal conversion characteristics when otherwise.

With the measuring circuit of the invention, the physiological quantity detection signals obtained in the process of giving the same massage to the same body part may result from the different kinds of signal conversion characteristics of the detection circuit, but insofar as these signals are included in the effective output range of one kind of conversion characteristics, a series of physiological quantity data in the process is produced based on the detection signals converted by the same kind conversion characteristics. Thus, detection of physiological quantities due to a changeover of signal conversion characteristics is suppressed to prevent impairment of measuring accuracy due to the characteristics changeover.

Stated more specifically, the physiological quantity sensor is a skin temperature sensor for measuring skin temperature, and the physiological quantity detection circuit has two kinds of signal conversion characteristics respectively for low temperatures and high temperatures which partly overlap each other in the temperature range to be measured. In this case, the signal processing circuit produces a series of items of skin temperature data in the process of giving the same massage to the same body part based only on physiological quantity detection signals resulting from the low-temperature signal conversion characteristics when said resulting detection signals are all included within the effective output range of the low-temperature signal conversion characteristics, or to produce a series of items of skin temperature data in the process based on physiological quantity detection signals resulting from the two kinds of signal conversion characteristics for high and low temperatures when otherwise.

The physiological quantity sensor is a perspiration quantity sensor for measuring the resistance value between a pair of electrodes, and the physiological quantity detection circuit has two kinds of signal conversion characteristics respectively of low gain and high gain which overlap each other in the range of resistance values to be measured. In this case, the signal processing circuit produces a series of items of perspiration quantity data in the process of giving the same massage to the same body part based only on physiological quantity detection signals resulting from the high-gain signal conversion characteristics when said resulting detection signals are all included within the effective output range of the high-gain signal conversion characteristics, or to produce a series of items of perspiration quantity data in the process based on physiological quantity detection signals resulting from the low-gain signal conversion characteristics when otherwise.

The physiological quantity measuring circuit of the invention for use in the massage machine detects physiological quantity of the user with high accuracy, making it possible to accurately detect the psychological state of the user and to give an effective massage.

BRIEF DESCRIPTION OF THE DRAWINGS

FIG. 6 is a diagram for showing rules for judging psychological states from variations in living body information;

DETAILED DESCRIPTION OF EMBODIMENTS

Figure 1:
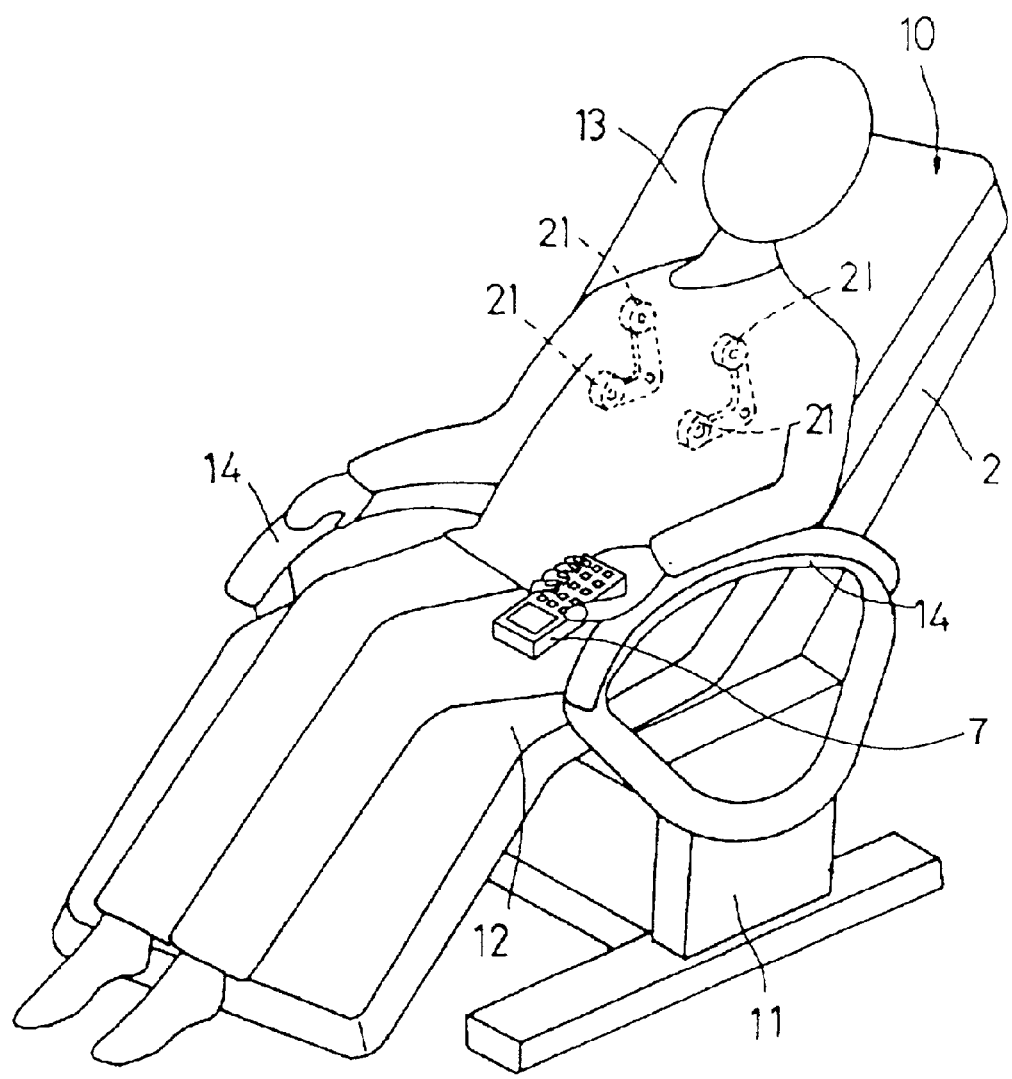
FIG. 1 is a perspective view showing a health care massage machine of the invention in use.

Embodiments of the invention will be described below in detail with reference to the drawings.
Massage Machine for Health Care With reference to FIG. 1, the massage machine of the present invention for health care comprises a chair body 10 including legs 11, a seat 12, a backrest 13 and a pair of opposite armrests 14, and a massage mechanism 2 having a plurality of therapeutic members 21 and incorporated into the chair body 10. The machine gives a massage to the human body by reciprocatingly moving the therapeutic members 21 up and down while vibrating these members 21. The massage machine can be operated by manipulating a remote controller 7 as shown.

Figure 2:
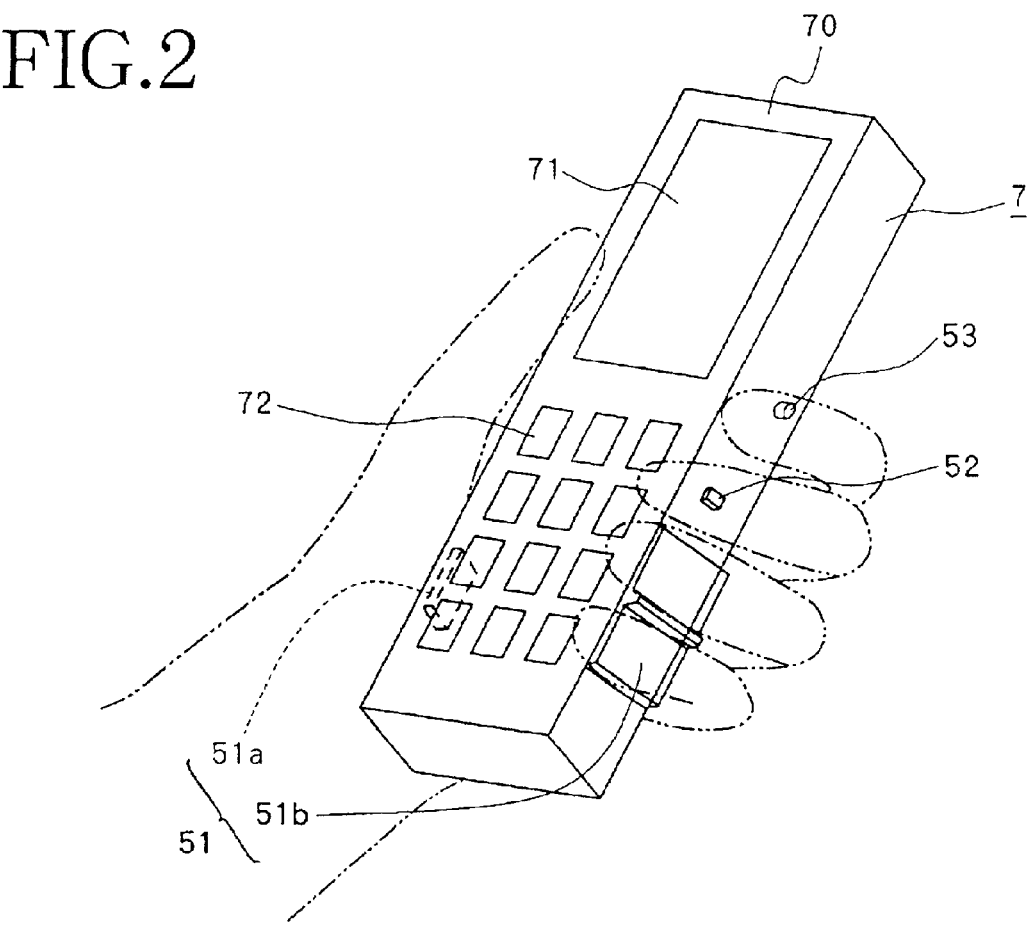
FIG. 2 is a perspective view showing the appearance of a remote controller.

With reference to FIG. 2, the remote controller 7 comprises a display 71 and a plurality of manual buttons 72 arranged on the front side of a vertical casing 70. Arranged on the right side face of the casing 70 are a pulse sensor 52 comprising a light-emitting element and light-receiving element, and a skin temperature sensor 53 comprising a thermistor. A GSR sensor 51 comprising a pair of electrodes 51$a$, 51$b$ is disposed on opposite side faces of the casing 70. When the controller 7 is grasped with the left hand as indicated in chain lines, the forefinger comes into contact with the skin temperature sensor 53, the middle finger with the pulse sensor 52, the ring finger and the little finger with the electrode 51$b$ of the GSR sensor 51 and the palm with the other electrode 51$a$ of the GSR sensor 51.

Figure 3:
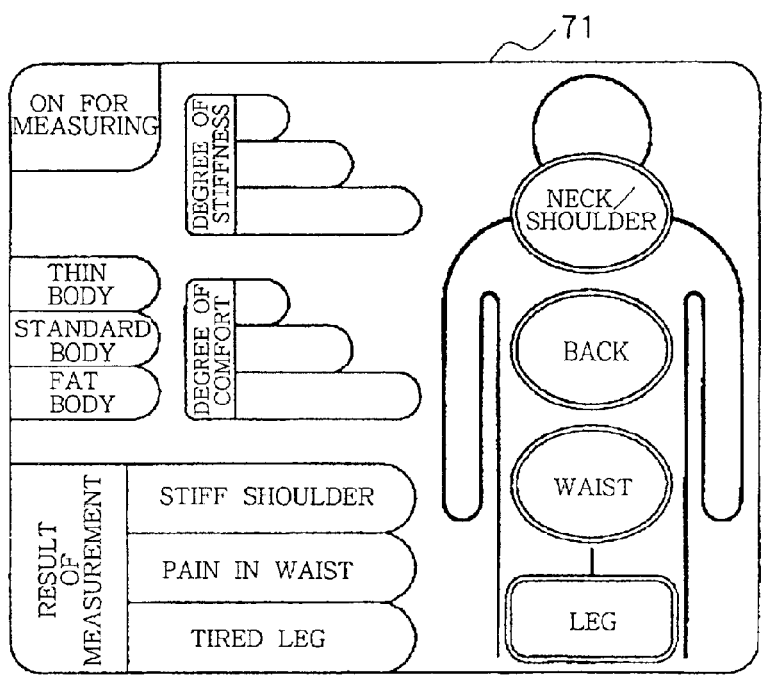
FIG. 3 is a diagram showing an exemplary representation on a display of the remote controller.
Figure 9:
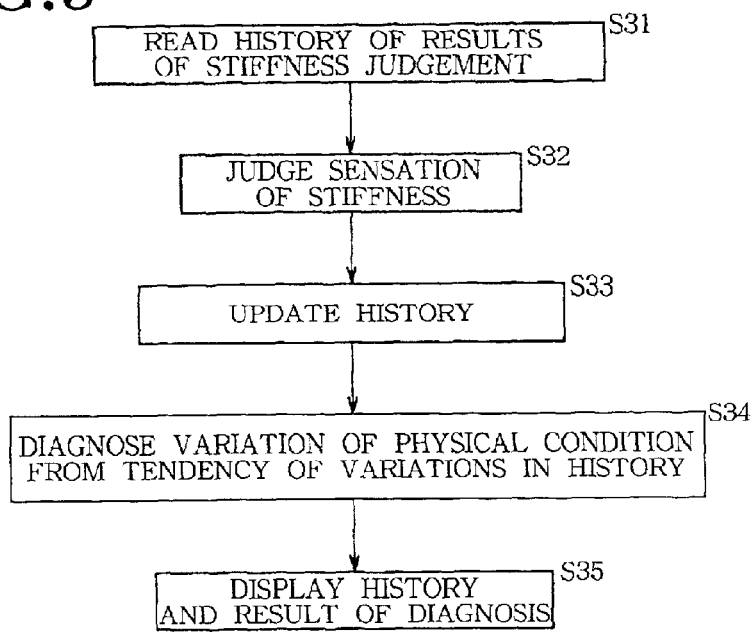
FIG. 9 is a flow chart showing a procedure for displaying a history of results obtained by judging the sensation of stiffness and result of diagnosis.

As seen in FIG. 3, the display 71 of the remote controller 7 shows the part being massaged, degree of stiffness, degree of comfort, position of the stiff part, etc. Further as shown in FIG. 9, variations in the count indicating the degree of stiffness are displayed upon a changeover of the screen.

Figure 4:
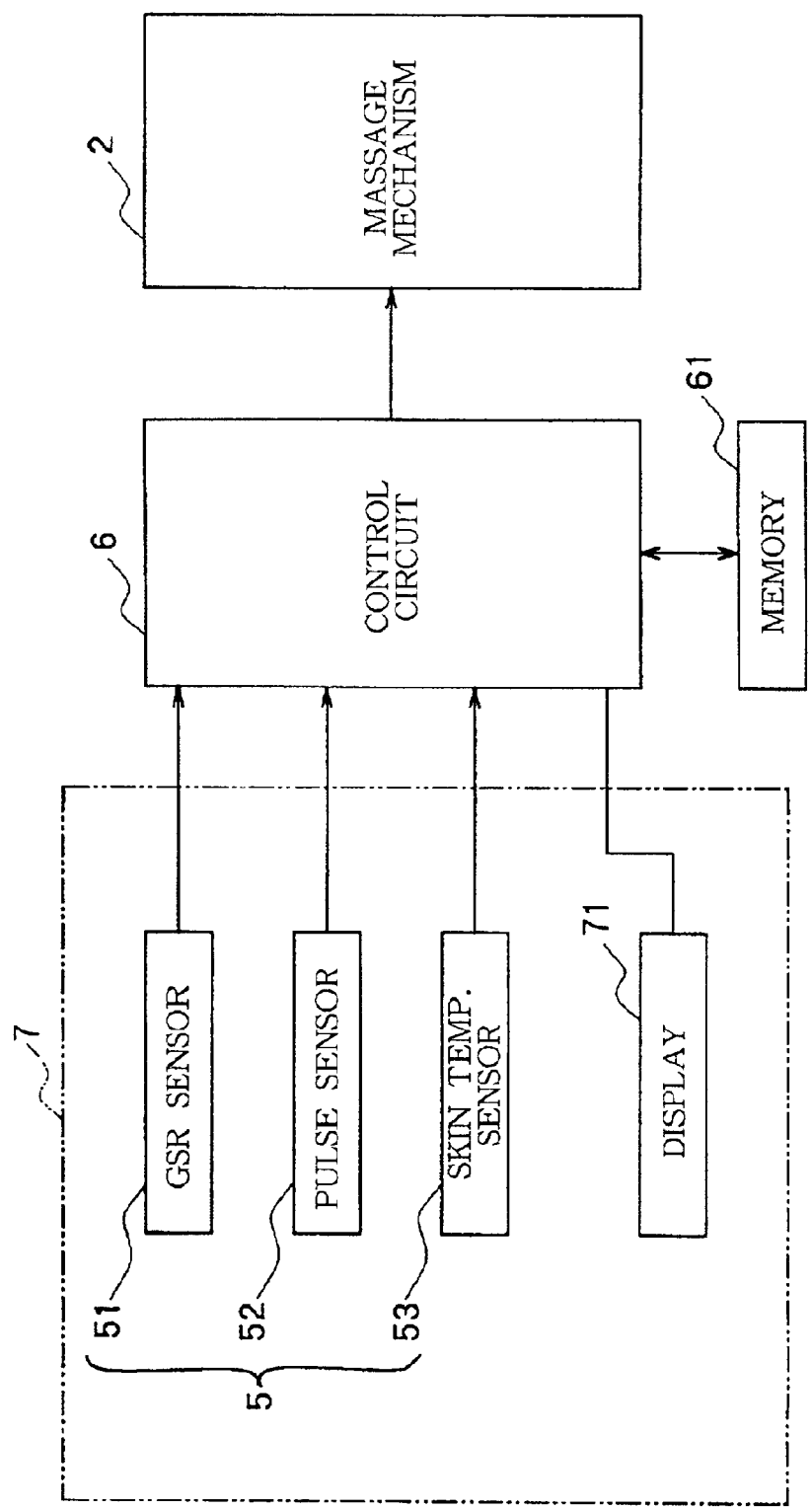
FIG. 4 is a block diagram showing the construction of a control system for the massage machine.

FIG. 4 shows the construction of a control system for the massage machine. A living body information sensor 5 comprising the GSR sensor 51, pulse sensor 52 and skin temperature sensor 53 is connected to input ports of a control circuit 6 comprising a microcomputer. The display 71 and the massage mechanism 2 are connected to output ports of the control circuit 6. A memory 61 is connected also to the control circuit 6.

Figure 5:
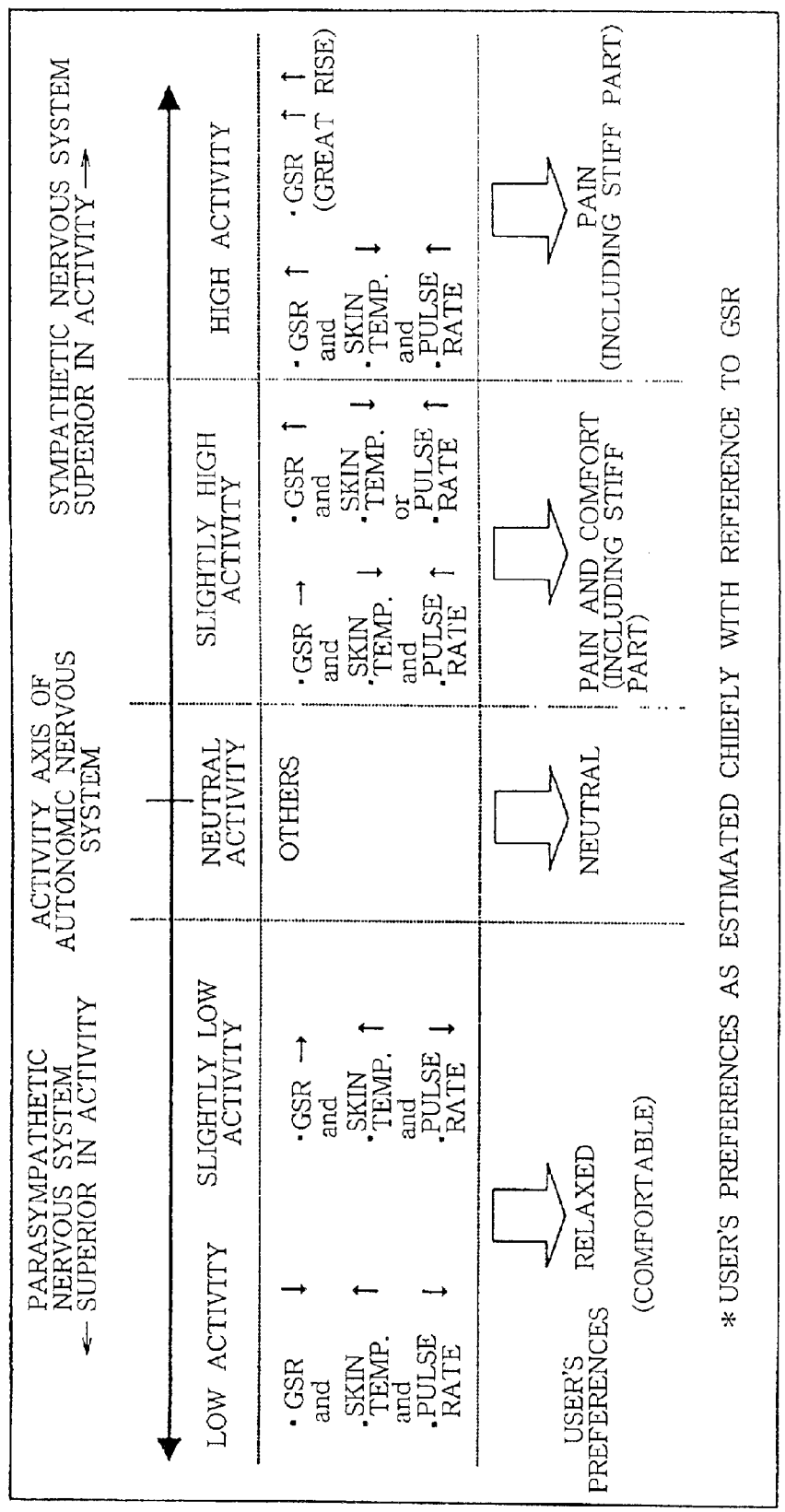
FIG. 5 is a diagram for illustrating the relationship between variations in living body information and psychological states.

FIG. 5 shows the relationship between the living body information detected by the living body information sensor 5, i.e., GSR, skin temperature and pulse rate and the psychological state of the person to be massaged (user). As illustrated, the GSR, skin temperature and pulse rate vary in different modes with the degree of activity of the autonomic nervous system. When the degree of activity is low, GSR and pulse rate lower and the skin temperature rises. When the degree of activity is slightly low, GSR remains unchanged, but the skin temperature rises and the pulse rate drops. If the degree of activity is slightly high, GSR rises from the constant level, the skin temperature lowers and the pulse rate rises. Further when the degree of activity is high, GSR greatly rises, the skin temperature drops and the pulse rate increases.

As the psychological states of the user in the event of such variations in the living body information, it is speculated that the user is in a relaxed comfortable state when the degree of activity is low, or that the user feels such a unique sensation as is experienced when massaged at a stiff part, feeling both pain and comfort as mingled therewith ("active" state), when the degree of activity is slightly high, or that the user feels a pain when the degree of activity is high. When the degree of activity is neutral, the user will presumably be in a neutral state, feeling neither comfort nor pain.

Figure 7:
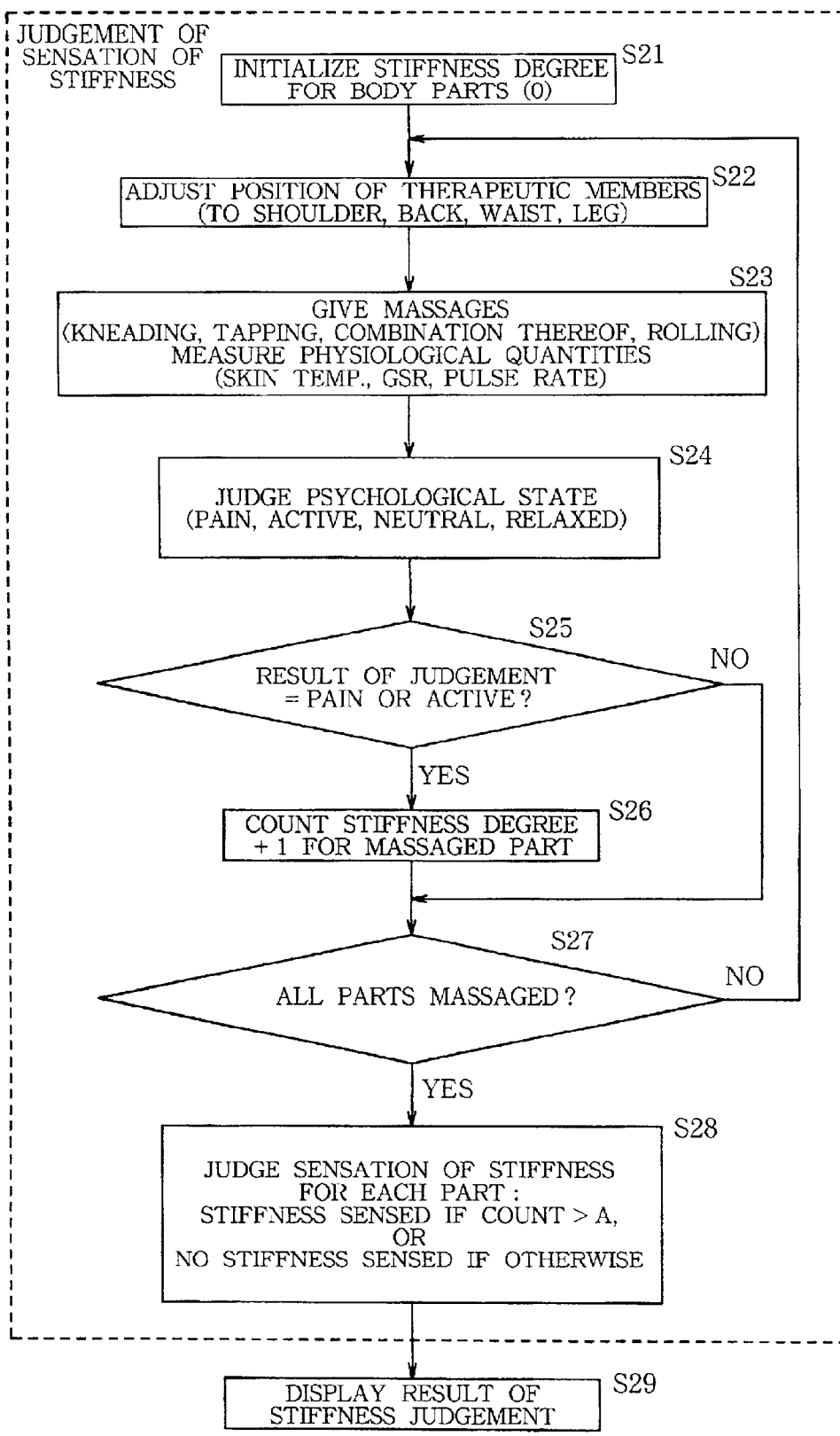
FIG. 7 is a flow chart for showing a procedure for judging the sensation of stiffness.

FIG. 7 shows a procedure to be executed by the control circuit 6 for judging the sensation of stiffness. The degree of stiffness for various body parts is initialized first in step S21, and the position of the therapeutic members is adjusted to one of the shoulder, back, waist and leg in step S22. Subsequently in step S23, various massages, i.e., kneading, tapping, combination of kneading and tapping, and rolling, are performed to measure physiological quantities (skin temperature, GSR and pulse rate) during these massage processes. The psychological state (pain, active, neutral or relaxed) is judged in step S24 by the procedure to be described below.

Subsequently, step S25 inquires whether the result of judgement is "pain" or "active," and if the answer is affirmative, the degree of stiffness of the massaged part is counted, followed by step S27, which inquires whether the massages have been performed for all the body parts.

If the inquiry of step S27 is answered in the negative, step S22 follows again. When the answer is affirmative, step S28 follows to judge the sensation of stiffness for each part. If the count of stiffness degree is greater than A serving as a threshold value, this is interpreted as indicating stiffness sensed. If otherwise, the judgement that no stiffness is sensed is made. The results of judgement thus made are stored in the memory 61. The sequence thereafter proceeds to step S29, in which the results of judgement are presented on the display 71.

Figure 8:
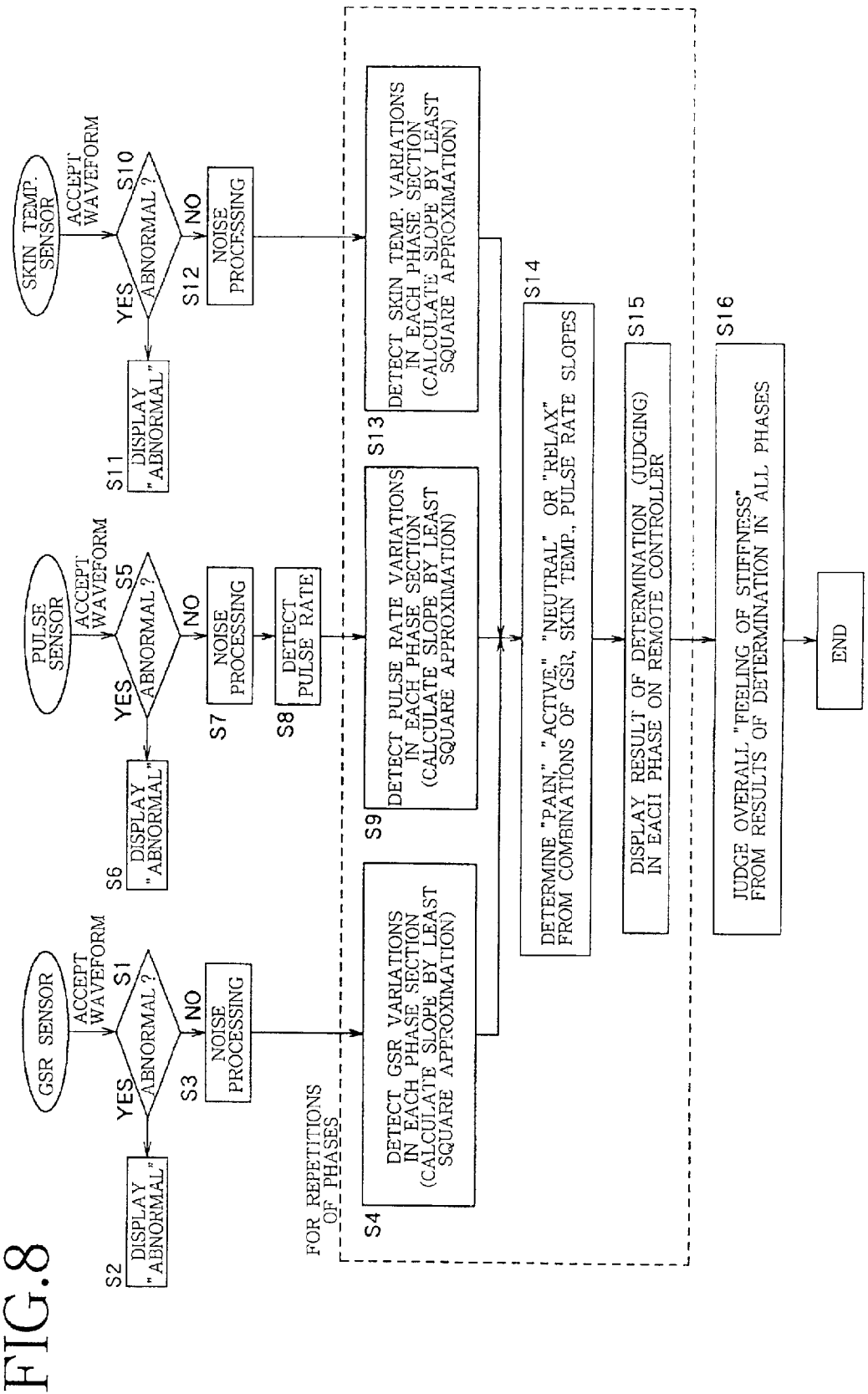
FIG. 8 is a flow chart showing a procedure for judging psychological states.

FIG. 8 shows a procedure for judging the psychological state (pain, active, neutral or relaxed). First in step S1, waveform is received from the GSR sensor to inquire whether the waveform, for example, resulting from release of the hand from the sensor is found abnormal. If the answer is affirmative, "abnormal" is displayed in step S2. When the waveform is found normal, step S3 follows for noise removal processing. The sequence then proceeds to step S4 to detect variations of GSR in each phase section (each massage movement). Slope can be detected, for example, by calculating the slope of GSR variations by least square approximation.

Further in step S5, waveform is received from the skin temperature sensor and checked for abnormality. If it is found abnormal, "abnormal" is displayed in step S6. When the waveform is found normal, step S7 follows for noise removal processing. The pulse rate is then detected in step S8. The sequence then proceeds to step S9 to detect variations of pulse rate in each phase section. Slope can be detected, for example, by calculating the slope of pulse rate variations by least square approximation.

Further in step S10, waveform is received from the skin temperature sensor and checked for abnormality. If it is found abnormal, "abnormal" is displayed in step S11. When the waveform is found normal, step S12 follows for noise removal processing. The sequence then proceeds to step S13 to detect variations of the skin temperature in each phase section. Slope can be detected, for example, by calculating the slope of skin temperature variations by least square approximation.

After the execution of steps S4, S9 and S13, step S14 follows to determine "pain," "active," "neutral" or "relaxed" from combinations of GSR variations $\Delta G$, skin temperature variations $\Delta T$ and pulse rate variations $\Delta H$ shown in FIG. 6. Incidentally, FIG. 6 shows the estimation of psychological states based on the relationship of FIG. 5 as formulated.

Subsequently step S15 of FIG. 8 displays on the remote controller the result of judgement of the psychological state in each phase (each massage movement). After repeating steps S4, S9, S13, S14 and S15 a number of times for the repetitions of all the phases, the sequence proceeds to step S16, in which an overall "sensation of stiffness" is judged from the results of judgement in all phases, and the final result is displayed on the display 71 to complete the procedure. The result of judgement in each phase is stored in the memory 61.

With the massage machine described, the remote controller 7 is manipulated to update the history of results of judgement of stiffness sensation and present on the display 71 the result obtained by diagnosing the condition of the user's health based on the history. FIG. 9 shows this procedure. The history of results of stiffness sensation judgement is read from the memory 61 first in step S31, the sensation of stiffness is judged in step S32, and the history is thereafter updated in step S33. The variation of physical condition of the user is diagnosed in step S34 based on the tendency of variations in the history. The history and the result of diagnosis are displayed in step S35.

Figure 10:
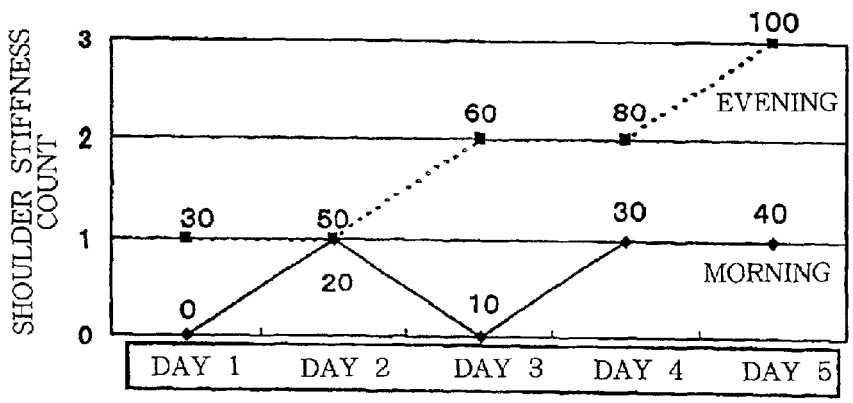
FIG. 10 is a graph showing variations in the count of degree of stiffness.

FIG. 10 shows an exemplary representation of tendency of variations in the history of results of stiffness sensation judgement. In the illustrated example, count values of degrees of stiffness in the shoulder in the morning (before work), as indicated in a solid line and count values of corresponding stiffness degrees in the evening (after work), indicated in a broken line show a rising tendency, revealing an increase in the sensation of shoulder stiffness especially in the evening. A high correlation found between the subjective values of shoulder stiffness degree and the count values thereof further shows that the method of judging the sensation of stiffness accordingly to the invention is reasonable.

Figure 11:
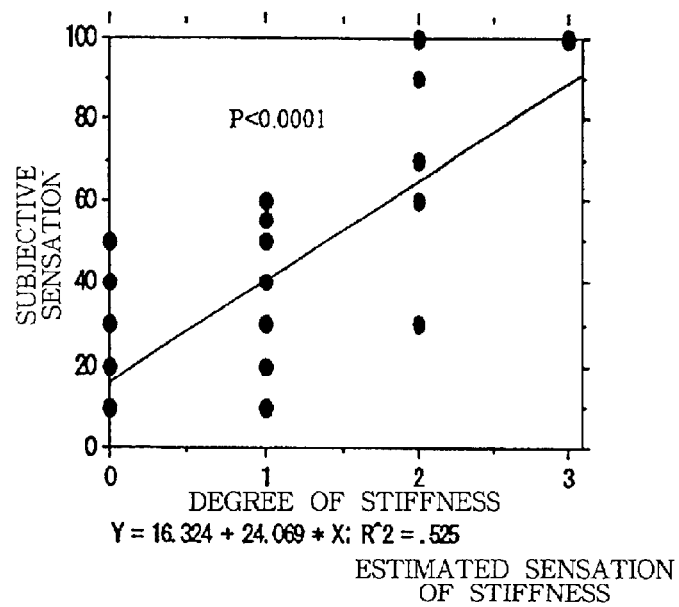
FIGS. 11($a$) and 11($b$) are graphs showing the results of regression analyses of subjective values and estimated values, respectively, of stiffness degrees.
Figure 11:
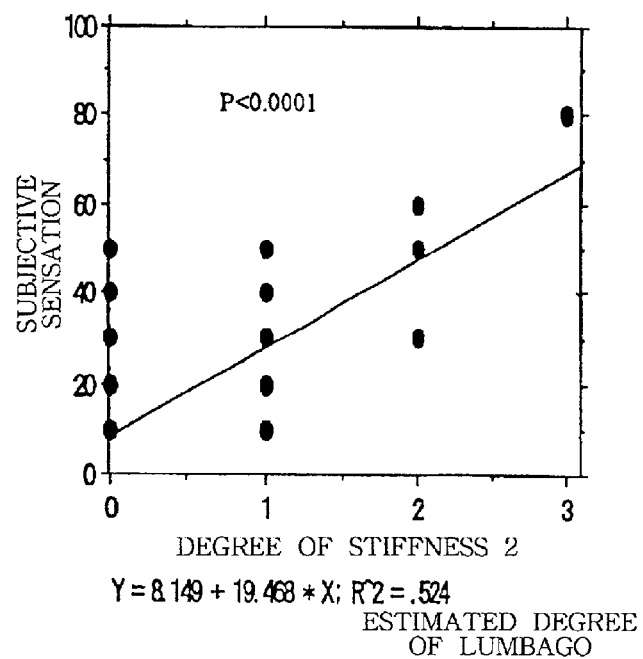

FIGS. 11(a) and 11(b) are graphs showing the results of regression analyses of subjective values (0 to 100) of stiffness degrees and estimated stiffness degrees (counts) for the sensation of shoulder stiffness and lumbago, respectively. These graphs also reveal a high correlation between the subjective values of stiffness degrees and the estimated values thereof, thus substantiating the reasonability of the stiffness sensation judging method of the invention.

Thus, the massage machine embodying the present invention for health care is adapted to diagnose variations in the physical condition of the user by massaging various body parts, for example, from the tendency of variations in the counts of stiffness in the shoulder as shown in FIG. 10. The result of diagnosis can be utilized as guidelines for health care.

Physiological Quantity Measuring Circuit for Massage Machine

Figure 12:
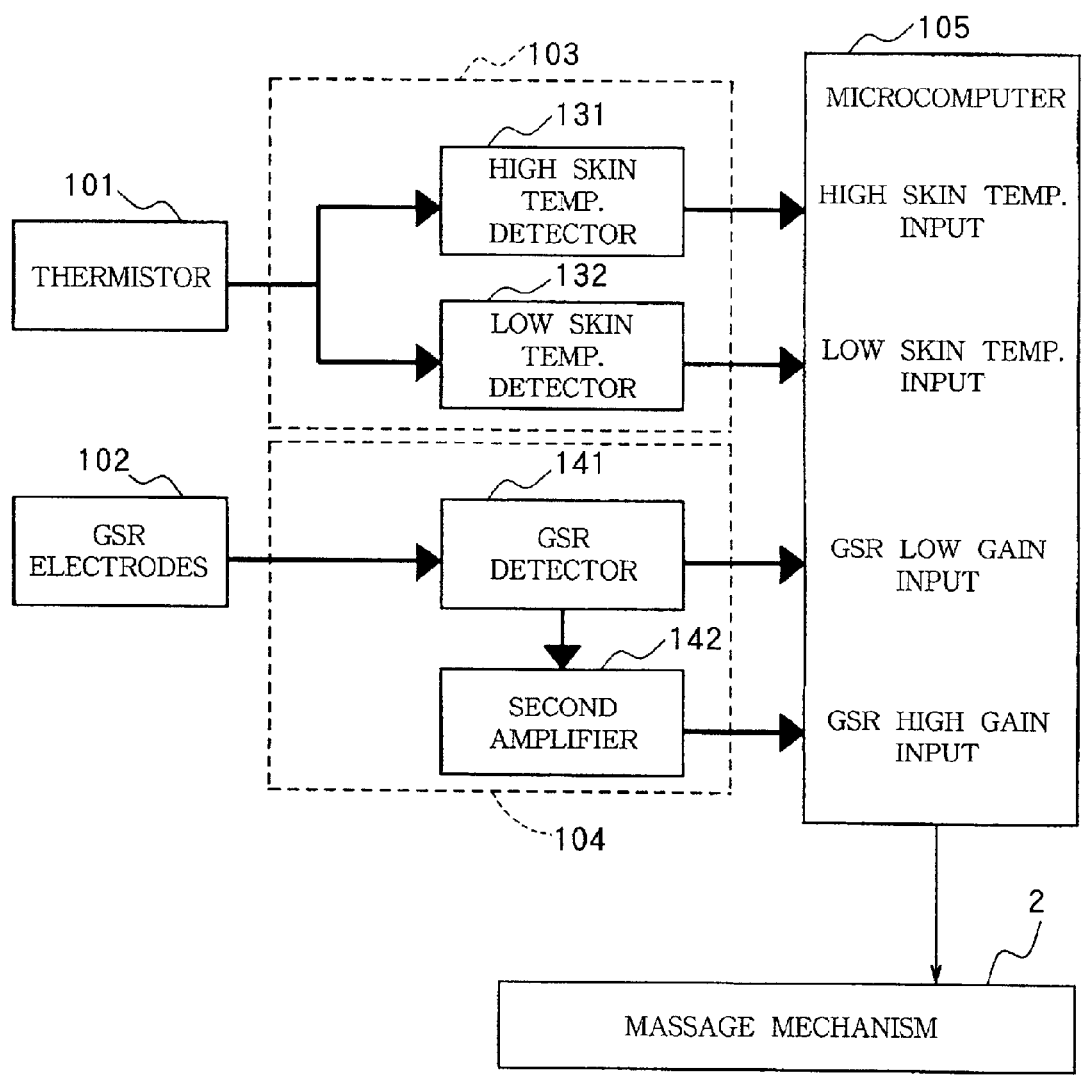
FIG. 12 is a block diagram showing the construction of a physiological quantity measuring circuit for use in the massage machine of the invention.

With the massage machine of the present invention, the massage mechanism 2 has its operation controlled by a microcomputer 105 as shown in FIG. 12. A thermistor 101 for measuring the skin temperature and GSR electrodes 102 for measuring the quantity of perspiration are worn, for example, on finger tips of the user. The thermistor 101 is connected via a skin temperature detection circuit 103 to the microcomputer 105. The GSR electrodes 102 are connected to the microcomputer 105 via a GSR detection circuit 104. The skin temperature detection circuit 103 comprises a high skin temperature detector 131 and a low skin temperature detector 132. The GSR detection circuit 104 comprises a GSR detector 141 and a second amplifier 142.

Figure 13:
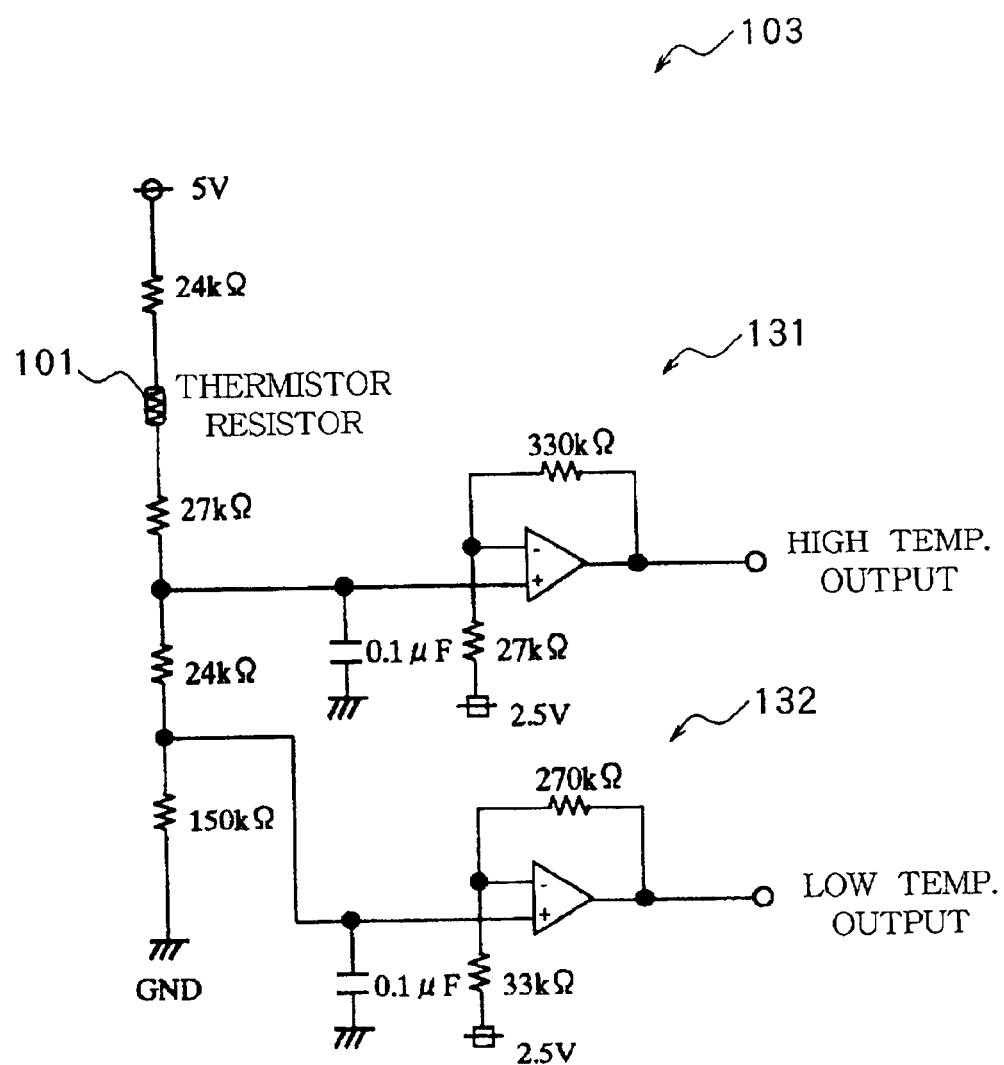
FIG. 13 is a diagram showing the construction of a skin temperature detection circuit.

FIG. 13 shows the construction of the skin temperature detection circuit 103 in detail. Variations in the resistance value of the thermistor 101 due to variations in skin temperature are converted to voltage variations by the high skin temperature detector 131 and low skin temperature detector 132, which produce a high temperature detection signal and a low temperature detection signal, respectively.

Figure 15:
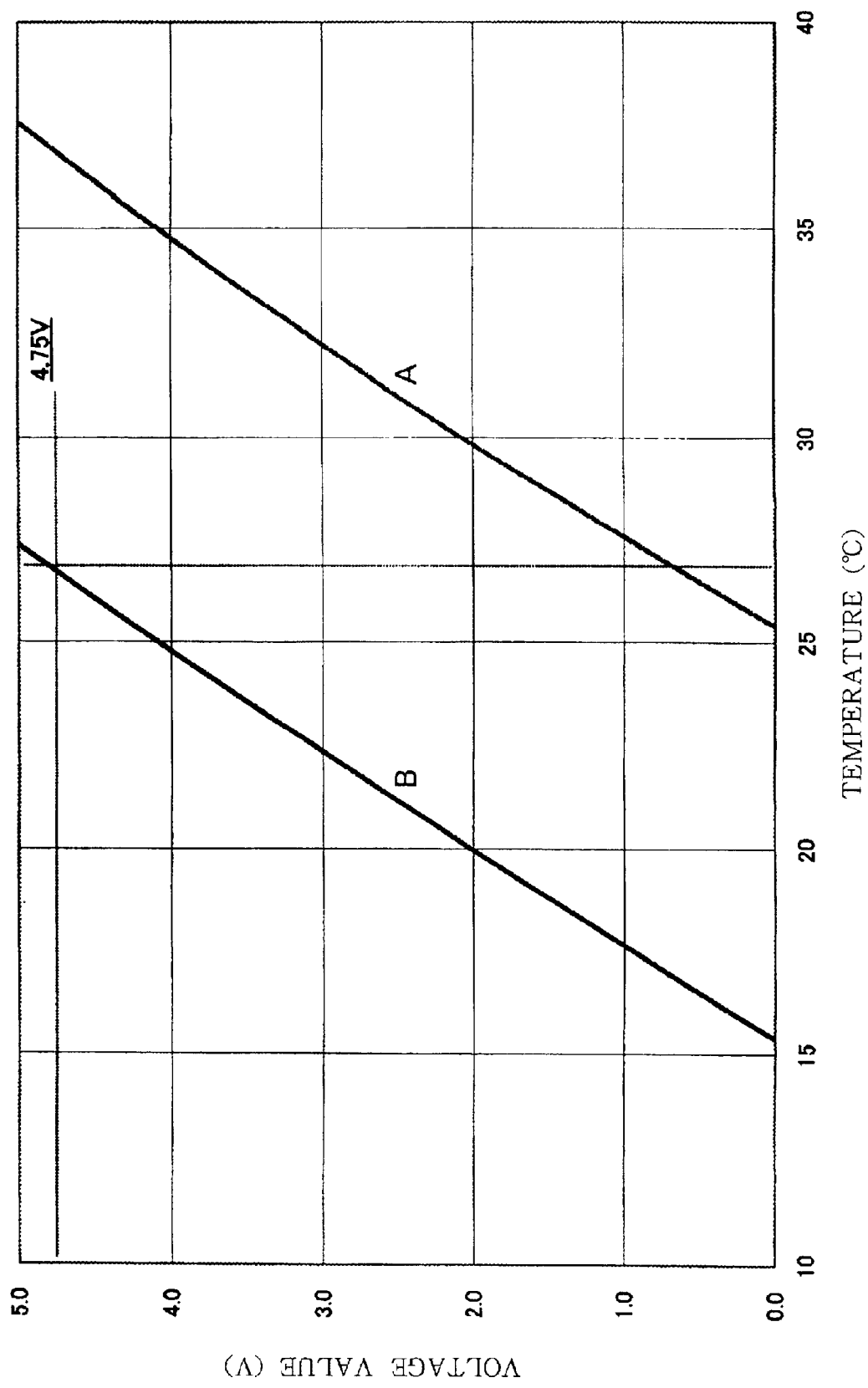
FIG. 15 is a graph showing the signal conversion characteristics of the skin temperature detection circuit.

FIG. 15 shows the relationship (signal conversion characteristics) A between the input signal (temperature) of the high temperature detector 131 of the circuit 103 and the output signal (voltage) thereof, and the relationship (signal conversion characteristics) B between the input signal (temperature) of the low temperature detector 132 of the circuit 103 and the output signal (voltage) thereof. The two kinds of signal conversion characteristics overlap each other at around 27° C. The two kinds of signal conversion characteristics A, B for high temperatures and low temperatures each provide effective output voltages in the range of up to 4.75 V, and are greater in slope than in the prior art.

Figure 14:
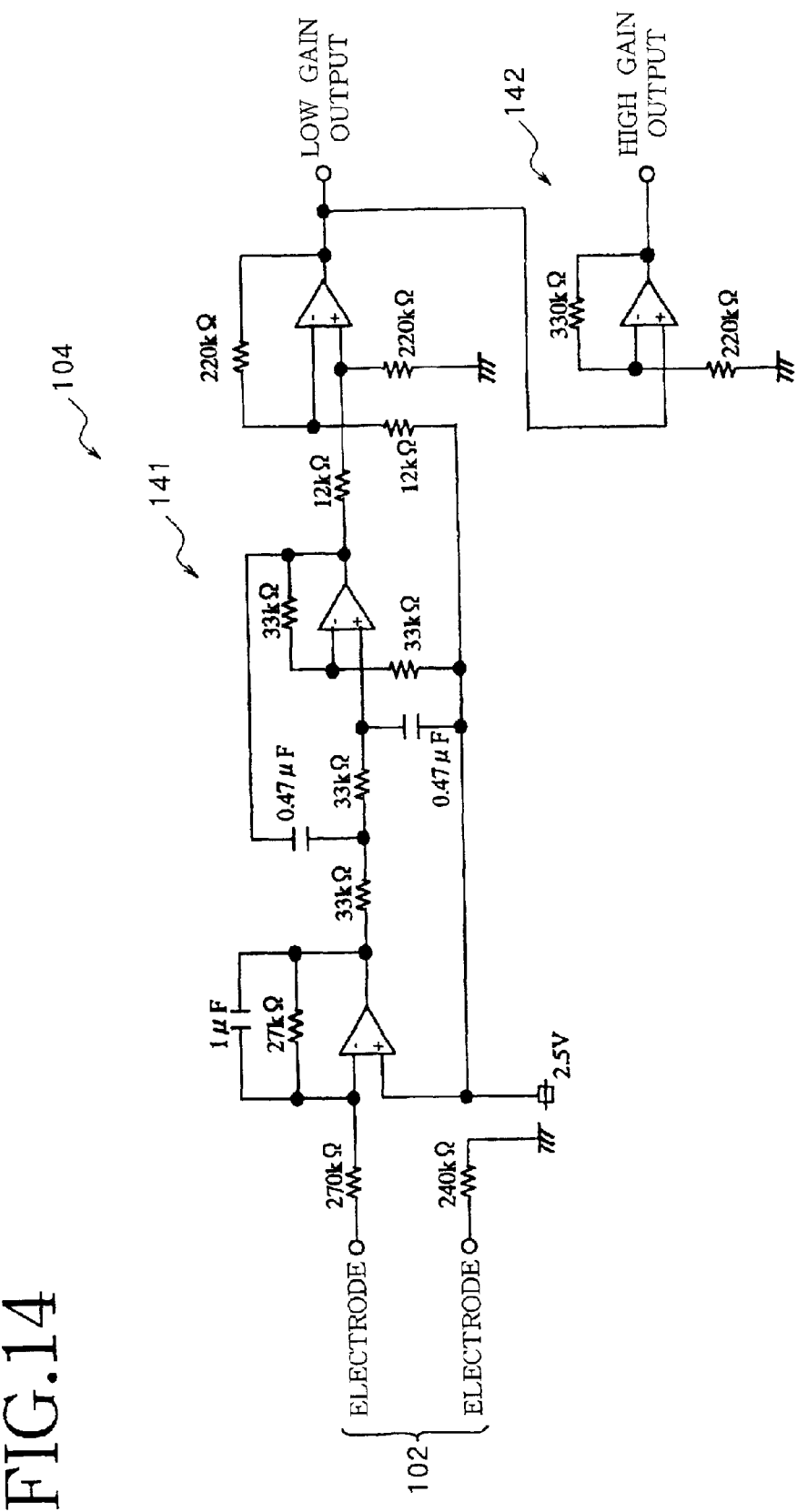
FIG. 14 is a diagram showing the construction of GSR detection circuit.

FIG. 14 shows the construction of the GSR detection circuit 104 in detail. Variations in the resistance value between the pair of GSR electrodes 102 due to variations in the quantity of perspiration are converted to voltage variations first by the GSR detector 141, and the voltage variations are further amplified by the second amplifier 142. Thus, these components 141, 142 deliver a low gain GSR detection signal and a high gain GSR detection signal, respectively.

Figure 16:
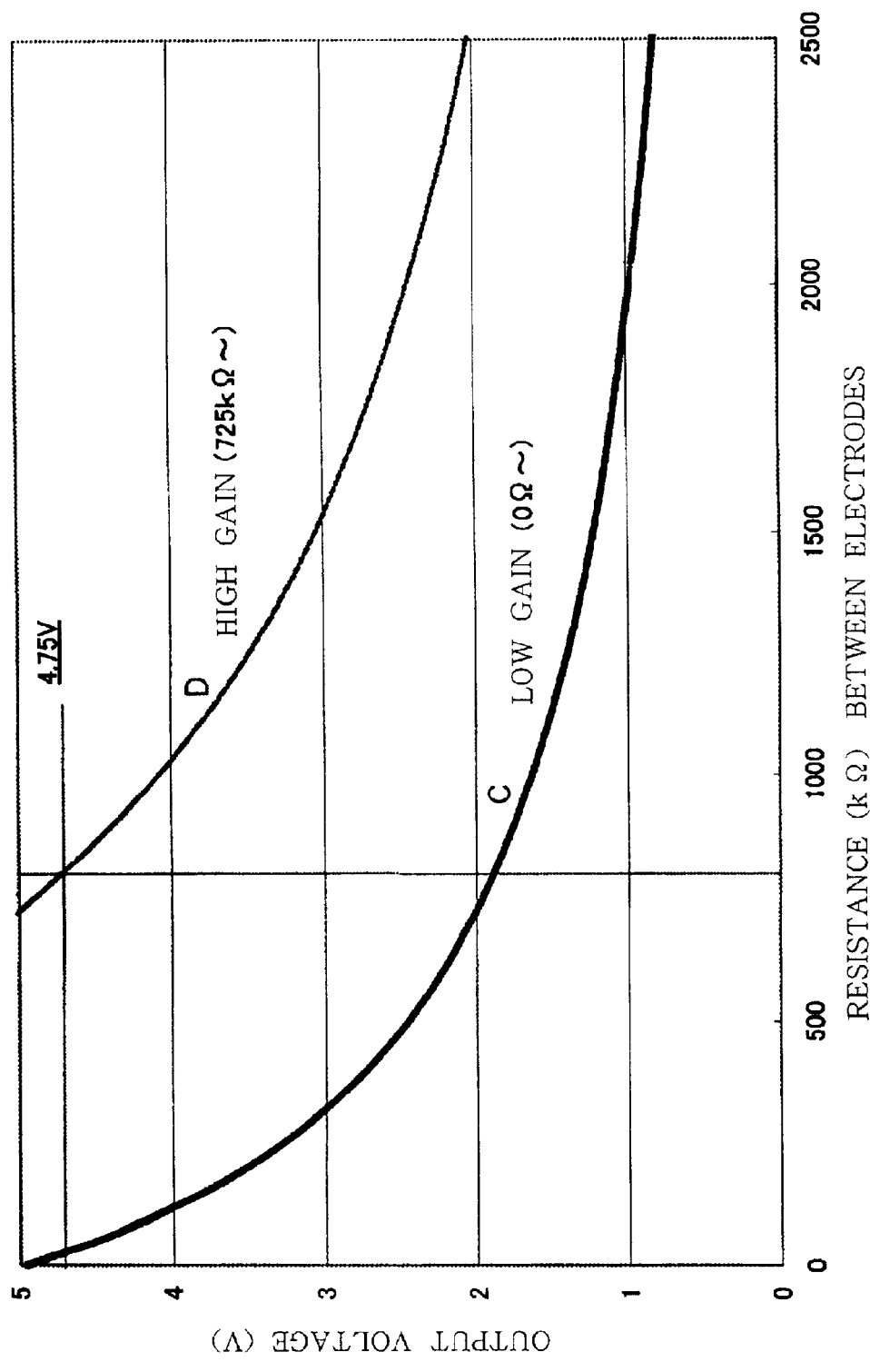
FIG. 16 is a graph showing the signal conversion characteristics of the GSR detection circuit.

FIG. 16 shows the relationship (signal conversion characteristics) C between the input signal (resistance) of the GSR detector 141 of the GSR detection circuit 104 and the output signal (voltage) thereof, and the relationship (signal conversion characteristics) D between the input signal (resistance) of the second amplifier 142 of the circuit 104 and the output signal (voltage) thereof. The two kinds of signal conversion characteristics overlap each other at resistance values of not lower than 725 kΩ. The two kinds of low gain and high gain signal conversion characteristics C, D each provide effective output voltages in the range of up to 4.75 V. Within the range of effective output voltages, the high gain characteristics exhibit a greater slope than the low gain characteristics.

Figure 17:
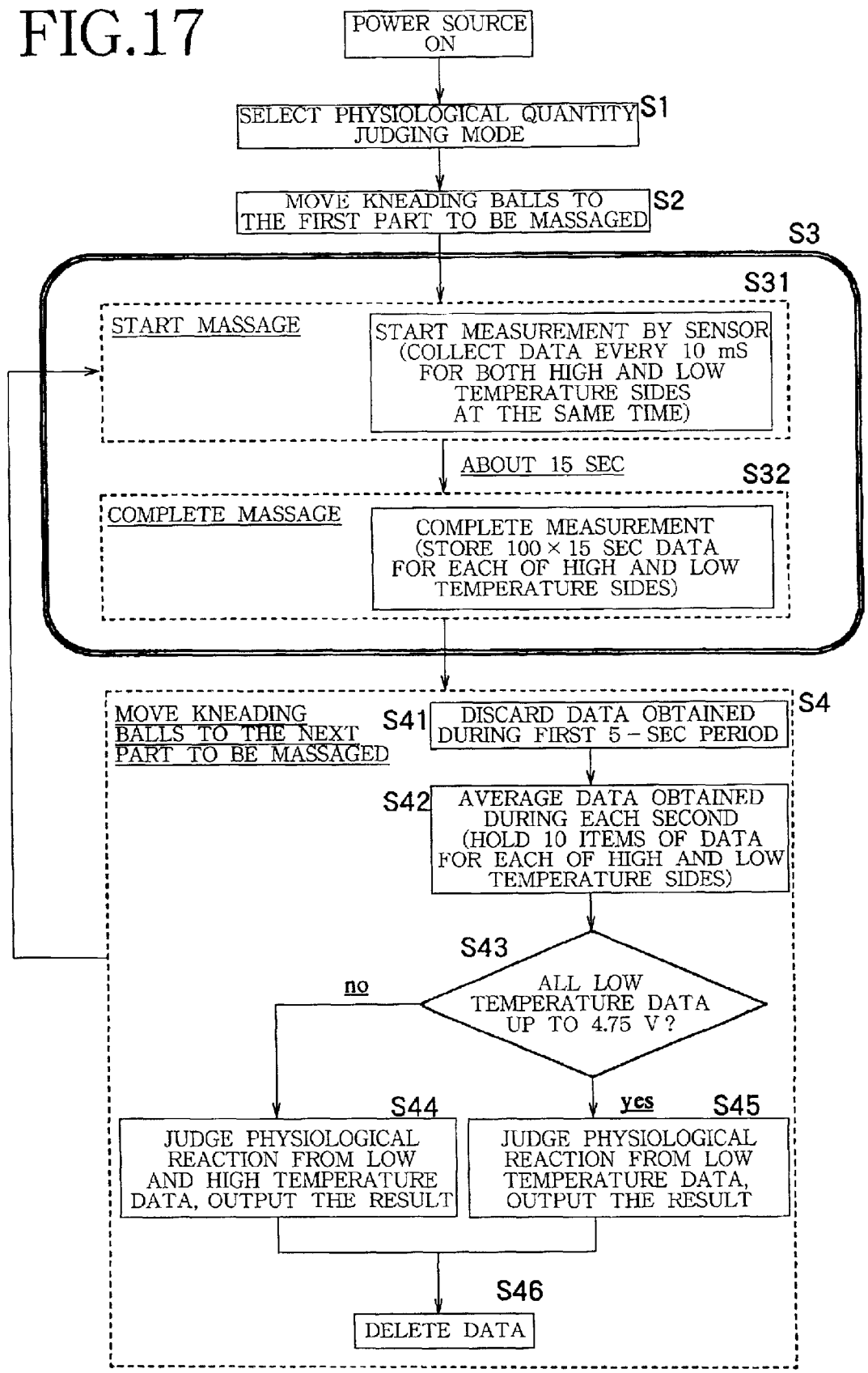
FIG. 17 is a flow chart showing a procedure for measuring the skin temperature.

FIG. 17 shows the skin temperature measuring procedure to be performed by the microcomputer 105. When a physiological quantity judging mode is selected first in step S1, the kneading balls are moved to the first part to be massaged in step S2, and a data collecting procedure is thereafter performed in step S3. Stated more specifically, when a particular massage is started on the specified part, step S31 follows to start to measure the skin temperature by the skin temperature sensor (thermistor), and data (voltage values) obtained by the signal conversion characteristics for high temperatures and the signal conversion characteristics for low temperatures is collected at an interval of 10 mS. When one massage operation is completed upon lapse of about 15 sec, the measurement is completed in step S32, and 1500 items of data for each of the high temperature side and the low temperature side are stored in the memory.

Subsequently, during the shift of the kneading balls to the next part to be massaged, the data is processed in step S4. First, the data obtained during the first 5-sec period is discarded in step S41. In step S42, an average is obtained from the data available during each second to hold ten items of data for each of the high and low temperature sides. An inquiry is then made in step S43 as to whether the items of low-temperature data are all in the effective output voltage range of up to 4.75 V shown in FIG. 15. When the answer is affirmative, step S45 follows to detect variations in skin temperature based on the low-temperature data, detect the physiological reaction based on the result of detection and output the final result.

If the answer to the inquiry of step S43 is negative, on the other hand, the data within the effective output range is selected from among the low-temperature and high-temperature data in step S44 to obtain a series of data items to detect variations in skin temperature from the data, detect the physiological reaction from the result of detection and output the final result. All the data is thereafter deleted in step S46. Simultaneously with the start of a massage on the next part to be massaged, step S31 follows again to start measurement with the skin temperature sensor.

Figure 18:
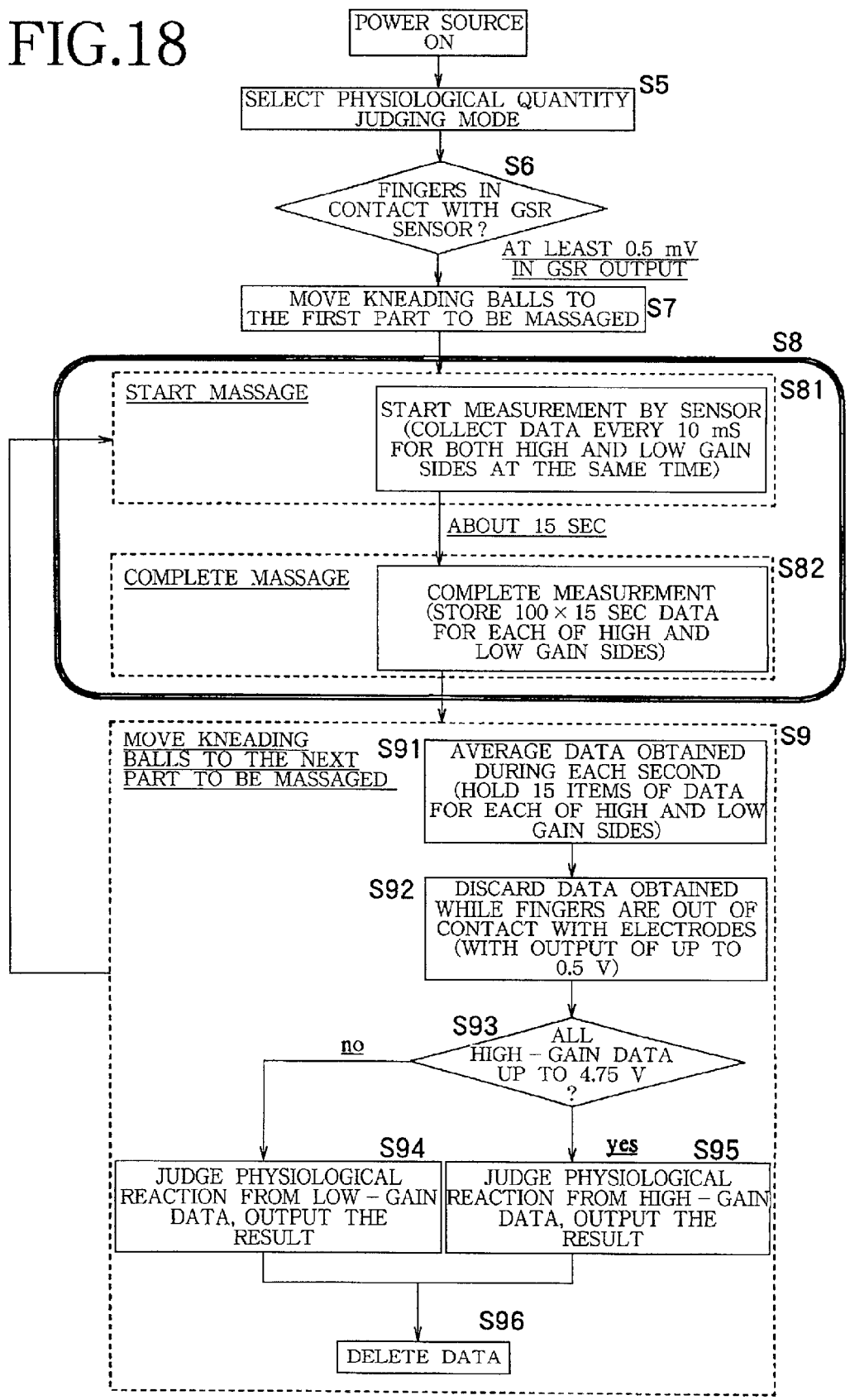
FIG. 18 is a flow chart showing a procedure for measuring GSR.

FIG. 18 shows the GSR measuring procedure to be performed by the microcomputer 105. When a physiological quantity judging mode is selected first in step S5, step S6 checks whether fingers comes into contact with the GSR electrodes with reference to GSR output. If the output is not smaller than 0.5 mV, this indicates contact. The kneading balls are moved to the first part to be massaged in step S7, and a data collecting procedure is then performed in step S8. Stated more specifically, when a particular massage is started on the specified part, step S81 follows to start to measure GSR by the GSR sensor (GSR electrodes), and data (voltage values) obtained by the high-gain signal conversion characteristics and the low-gain signal conversion characteristics is collected at an interval of 10 mS. When the massage operation is completed upon lapse of about 15 sec, the measurement is completed in step S82, and 1500 items of data for each of the high gain side and the low gain side are stored in the memory.

Subsequently, during the shift of the kneading balls to the next part to be massaged, the data is processed in step S9. First in step S91, an average is obtained from the data available during each second to hold 15 items of data for each of the high and low gain sides. Discarded in the next step S92 is the data obtained during the period (with an output of up to 0.5 V) in which the finger is out of contact with the electrodes. An inquiry is then made in step S93 as to whether the items of high-gain data are all in the effective output voltage range of up to 4.75 V shown in FIG. 16. When the answer is affirmative, step S95 follows to detect variations in GSR based on the high-gain data, detect the physiological reaction based on the result of detection and output the final result. If the answer to the inquiry of step S93 is negative, on the other hand, step S94 follows to detect variations in GSR based on the low-gain data, detect the physiological reaction from the result of detection and output the final result.

All the data is thereafter deleted in step S96. Simultaneously with the start of a massage on the next part to be massaged, step S81 follows again to start measurement with the GSR sensor.

In measuring the skin temperature, the massage machine described above uses signal conversion characteristics having high sensitivity for both high temperatures and low temperatures as shown in FIG. 15. For measurement in the region of high temperatures, high-temperature signal conversion characteristics are used, while for measurement in the region of low temperatures, low-temperature signal conversion characteristics are used. This ensures higher measurement accuracy than in the prior art.

Further in measuring GSR, high-gain signal conversion characteristics are used in the region of high resistances in addition to low-gain signal conversion characteristics as shown in FIG. 16 to assure higher measurement accuracy than conventionally. In giving the same massage to the same part for the measurement of skin temperature and GSR, physiological quantity detection data obtained by one kind of signal conversion characteristics is used to measure variations in the skin temperature and GSR insofar as this is feasible. This obviates errors to be involved in a changeover of signal conversion characteristics.

What is claimed is:

1. A physiological quantity control and measuring circuit for a massage machine, the circuit detecting a physiological quantity of the person massaged and controlling the massage operation of the machine based on variations in the physiological quantity, the measuring circuit comprising:

at least one sensor, sensing a single physiological quantity;

a detection and signal processing circuit, for producing physiological quantity data based on a signal obtained from the sensor, comprising a plurality of signal converters each adapted to receive an input signal from the sensor and deliver a respective output signal corresponding to the single physiological quantity, the signal converters exhibiting respective different signal conversion characteristics which are different in the relationship of the output signal to the input signal, the different signal conversion characteristics overlapping each other in an input range of the input signal, the detection and signal processing circuit being operable to produce data to control the massage operation based on the output signal, regardless of how many of the signal converters are used to convert the input signal into the output signal.

2. The physiological quantity control and measuring circuit according to claim 1, wherein the sensor is a skin temperature sensor for measuring skin temperature, and the detection and signal processing circuit includes two kinds of the signal conversion characteristics respectively for low temperatures and high temperatures which partly overlap each other in the temperature range to be measured.

3. The physiological quantity control and measuring circuit according to claim 2, wherein the signal processing circuit produces a series of items of skin temperature data in the process of giving the same massage to the same body part based only on physiological quantity detection signals resulting from the low-temperature signal conversion characteristics when said resulting detection signals are all included within the effective output range of the low-temperature signal conversion characteristics, or to produce a series of items of skin temperature data in the process based on physiological quantity detection signals resulting from the two kinds of signal conversion characteristics for high and low temperatures when said resulting detection signals are not all included within the effective output range of the low-temperature signal conversion characteristics.

4. The physiological quantity control and measuring circuit according to claim 1, wherein the sensor is a perspiration quantity sensor for measuring the resistance value between a pair of electrodes, and the detection circuit includes two kinds of the signal conversion characteristics respectively of low gain and high gain which overlap each other in the range of resistance values to be measured.

5. The physiological quantity control and measuring circuit according to claim 4, wherein the signal processing circuit produces a series of items of perspiration quantity data in the process of giving the same massage to the same body part based only on physiological quantity detection signals resulting from the high-gain signal conversion characteristics when said resulting detection signals are all included within the effective output range of the high-gain signal conversion characteristics, or to produce a series of items of perspiration quantity data in the process based on physiological quantity detection signals resulting from the low-gain signal conversion characteristics when said resulting detection signals are not all included within the effective output range of the high-gain signal conversion characteristics.

* * * * *